United States Patent [19]

Wijayarathna et al.

[11] Patent Number: 4,563,181

[45] Date of Patent: Jan. 7, 1986

[54] FUSED FLEXIBLE TIP CATHETER

[75] Inventors: Bandula Wijayarathna, Friendswood, Tex.; Ronald M. Hopkins, Chesterfield, Mo.

[73] Assignee: Mallinckrodt, Inc., St. Louis, Mo.

[21] Appl. No.: 467,939

[22] Filed: Feb. 18, 1983

[51] Int. Cl.[4] ............................................. A61B 6/00
[52] U.S. Cl. ................................ 604/280; 128/656; 128/658
[58] Field of Search ...................... 128/654, 656–658, 128/207.14, 207.15; 604/43, 45, 93, 96, 103, 264, 280–284, 95, 270; 156/283–331.8; 428/198, 200–206; 525/408, 419, 934

[56] References Cited

U.S. PATENT DOCUMENTS

| | | | |
|---|---|---|---|
| 4,034,015 | 7/1977 | Hedrick et al. | 525/420 |
| 4,265,848 | 5/1981 | Rüsch | 264/130 |
| 4,368,090 | 1/1983 | Mumcu et al. | 156/283 |
| 4,385,635 | 5/1983 | Ruiz | 128/658 |
| 4,419,095 | 12/1983 | Nebergall et al. | 604/96 |

*Primary Examiner*—C. Fred Rosenbaum
*Assistant Examiner*—Mario Costantino
*Attorney, Agent, or Firm*—Bernard, Rothwell & Brown

[57] ABSTRACT

An intravascular catheter, such as an angiography catheter, has a tubular body portion formed from a nylon such as nylon-11 which has strength and stiffness characteristics providing excellent torqueability, burst strength, and longitudinal rigidity. A soft tubular tip is fused to the end of the body portion to form a continuous tubular catheter. The soft tip is formed from a blend of the nylon of the body portion with an ester linked polyether-polyamide co-polymer which is soft and rubbery to render the tip soft to avoid injury to a blood vessel.

10 Claims, 2 Drawing Figures

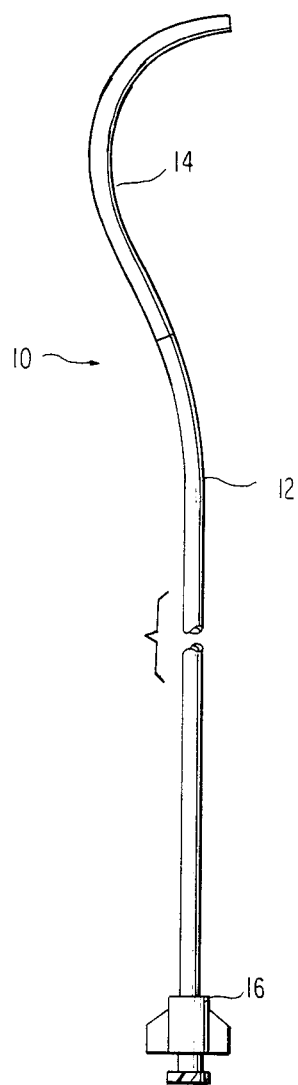
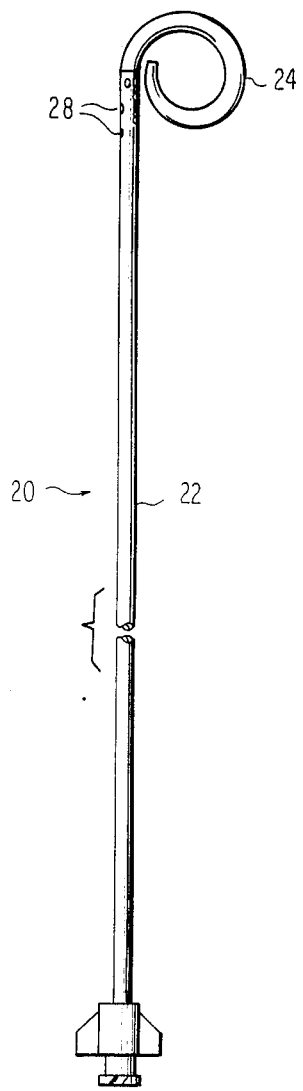
FIG. 1
FIG. 2

FUSED FLEXIBLE TIP CATHETER

BACKGROUND OF THE INVENTION

1. Field of the Invention

The present invention relates to catheters which are inserted into blood vessels and used to inject radiopaque dyes or to otherwise aid in medical treatment of a human or mammal.

2. Description of the Prior Art

The prior art contains a number of catheters designed for intravascular use in the treatment of disease including the injection of radiopaque dye into a blood vessel. Generally these catheters include a relatively stiff and strong body portion having a soft tip portion on the leading end. The stiff body portion is required to provide torqueability, burst pressure strength, and longitudinal rigidity or column strength for advancing the catheter in the vessel. Torqueability is required to enable the catheter to be twisted so a curved tip may be directed into a desired vessel. Burst strength is required to permit injection of fluids under pressure without ballooning or bursting of the catheter wall. Longitudinal rigidity or column strength is necessary to permit advancement of the catheter in a vessel by pushing on an exterior end of the catheter. The soft tip is necessary to avoid trauma and injury to the blood vessel walls which can be caused if the relatively stiff polymeric material is used in the tip portion.

Angiography catheters having a stiff body portion have been formed in the past by forming the polymer body portion with a braid to produce the desired stiffness, and either leaving the braid out during the forming of the tip portion or fusing a soft tip of the same or a similar polymer to the braided body portion. Additionally, angiography catheters have been constructed by coextruding inner and outer tubular polymer materials in the body portion with a soft polymer material extending beyond the stiff polymer tubular portion to form a soft tip portion. In catheters having soft tips which are fused, the polymer of the body portion and the polymer of tip portion must be substantially the same chemically since it has heretofore been impossible to fuse a soft polymer to a rigid polymer which is chemically substantially different.

Prior art catheters have been made from a variety of polymeric materials including polyurethane, polyethylene, nylon and PVC. Nylon, such as nylon-11, is a polymer that provides excellent stiffness characteristics when extruded into tubes of diameters in the range from 2 Fr. to 10 Fr. to produce catheters having excellent torqueability, burst strength characteristics, and longitudinal rigidity. The stiffness of the nylon tubes, however, results in a tip which is too stiff and which may cause vessel injury. Soft nylon materials generally contain plasticizers which may leach out while the catheter is in the vessel and thus are not suitable for forming soft tips.

SUMMARY OF THE INVENTION

The invention is summarized in an intravascular catheter including a tubular body which is formed from a nylon, and a soft tubular tip fused to the tubular body wherein the soft tip is formed from a material including a polyether-polyamide co-polymer having ester linkage to render the tip relatively more flexible and soft.

An object of the invention is to construct an intravascular catheter with a stiff body and soft flexible tip having improved properties and economics.

Another object of the invention is to utilize nylon and its superior characteristics for producing torqueability and column and burst strength in an intravascular catheter.

One advantage of the invention is that polyether-polyamide co-polymers are found sufficiently compatible with and fusible to nylon to enable fusing of a soft tip including such co-polymer onto a body of nylon to form a catheter with a stiff body and a flexible tip.

One feature of the invention is that the stiffness properties of nylon result in excellent torqueability and column and burst strength while softness and flexibility of polyether-polyamide co-polymer having ester linkage results in excellent tip softness and flexibility in intravascular catheters.

Other objects, advantages and features of the invention will be apparent from the following description of the preferred embodiment taken in conjunction with the accompanying drawings.

BRIEF DESCRIPTION OF THE DRAWINGS

FIG. 1 is a plan view with a portion broken away of a catheter constructed in accordance with the invention.

FIG. 2 is a plan view with a portion broken away of a modified catheter constructed in accordance with the invention.

DESCRIPTION OF THE PREFERRED EMBODIMENT

As shown in FIG. 1, one embodiment of the invention is in the form of a catheter indicated generally at 10 having a tubular body 12 and a soft tip 14 attached to one end of the body 12. Conveniently a luer 16 is attached to the other end of the tubular body 12. The tubular body 12 is formed from a nylon selected to have desired stiffness characteristics. The tip 14 is formed from a material which includes a polyether-polyamide copolymer having ester linkage in sufficient quantity to produce desired flexibility and softness in the tip to avoid damage to blood vessels in which the catheter is being inserted.

Nylon is a polymer that provides excellent stiffness characteristics. Extruded tubes of nylon in catheter dimensions, i.e. 2 Fr. to 10 Fr., have excellent torqueability, burst pressure strength, and longitudinal rigidity. The torqueability permits the catheter to be twisted or turned, while being inserted, to direct the tip, which is generally precurved, into a desired vessel. The burst strength permits fluids to be injected under pressure without ballooning or bursting of the catheter wall. The longitudinal rigidity or column strength of the catheter permits pushing of the catheter by one end without buckling or folding of the catheter within the vessel.

The soft tip 14 can be a tube which is formed from a blend of the nylon of the body 12 and the ester linkage co-polymer of polyether and polyamide, such as that commonly known as polyether block amide (PEBA). This co-polymer is a soft, rubbery polymeric material which is compatible with and fusible to nylon by the application of heat and pressure. This co-polymer is chemically represented as:

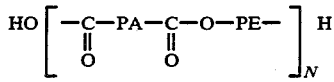

where PA is a polyamide and PE is a polyether and where N is an integer greater than 1 representing the number of blocks of co-polymer molecular units within the molecular formula of the co-polymer. The PEBA material has a wide range of flexibility, absence of plasticizers, high elastic memory and good mechanical properties thus making it ideal for catheter construction. For angiography applications, however, the co-polymer is too flexible and does not provide sufficient mechanical stability, which is often needed to maintain various curve shapes and configurations. Thus the nylon is blended with the copolymer in quantities to produce an increase in the strength and stiffness of the tip, but still maintaining substantial softness and flexibility necessary to avoid vessel trauma. The co-polymer of polyamide and polyether has a tensile strength in the range from 20 to 35 MPA, elongation of 200 to 700% and a shore hardness of 70A to 55D while the nylon-11 has a tensile strength from 6,000 to 10,000 PSI. Typically PEBA forms 50 to 70%, by weight, of the blend of polymer materials forming the tip 14 with the remainder being nylon-11. Other proportions of nylon and PEBA are possible to obtain desired catheter properties. One particular PEBA that has been found suitable is PEBAX from Rilsan.

Conveniently the tubular tip 14 is fused at one end thereof to the leading end of the body 12 by using heat and pressure. The tubes forming the body 12 and the tip 14 can be extruded into respective tubes in a conventional manner. These tubes, cut into desired lengths, are fused together in a butt-joint by using heat and pressure to form continuous tubular catheters. The tip 14 containing PEBA is found to form a strong bond to the end of the body 12 due to similar chemical properties of nylon and PEBA.

The present catheter offers substantial economical improvements. Utilizing a butt-welding or fusing technique between the tubular tip 14 and tubular body 12 eliminates the necessity for coextruding materials with braids and coaxial stiff polymer materials to form the stiffened body and flexible tip. Additionally the ability to adjust blending ratios of nylon and PEBA in the tip 14 enables great flexibility in producing a catheter with desired body stiffness and tip flexibility and softness. The performance of the present catheter has been found superior to that of catheters constructed in other manners.

In a modified catheter as illustrated generally at 20 in FIG. 2, a tubular body 12 has an attached pigtail type tip 24 which is fused or bonded to the distal end of the body 22. This embodiment differs from that of FIG. 1 by having holes 28 formed within the side wall of the body portion 22 adjacent to the tip 24. Thus liquid may be injected or blood may be withdrawn through the holes 28 adjacent to the tip 24.

Since many modifications, variations and changes in detail may be made to the above described embodiments, it is intended that all matter in the foregoing description and shown in the accompanying drawings be interpreted as illustrative and not in a limiting sense.

What is claimed is:

1. An intravascular catheter comprising
   a tubular body formed from a nylon having desired stiffness characteristics for torqueability, burst strength and longitudinal rigidity,
   a soft flexible tip having one end thereof fused on one end of the tubular body to form a catheter having a relatively stiff tubular body and a relatively soft flexible tip, and
   said tip being formed from a material including a polyether-polyamide co-polymer having ester linkage in sufficient quantities to render the material soft and flexible to avoid trauma to blood vessels.

2. An intravascular catheter as claimed in claim 1 wherein the nylon is nylon-11 and the polyether-polyamide co-polymer is polyether block amide.

3. An intravascular catheter as claimed in claim 1 wherein the polyether-polyamide co-polymer has the following formula

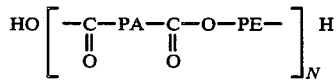

where PA is a polyamide, PE is a polyether, and N is an integer greater than 1.

4. An intravascular catheter as claimed in claim 1 wherein the material of the soft flexible tip consists of a blend of the nylon of the tubular body and polyether block amide.

5. An intravascular catheter as claimed in claim 4 wherein the nylon of the tubular body and the tip is nylon-11.

6. An intravascular catheter as claimed in claim 5 wherein the blend includes from 30 to 50% by weight nylon-11.

7. An intravascular catheter as claimed in claim 1 wherein the soft flexible tip is tubular and is butt-fused on the distal end of the tubular body.

8. An intravascular catheter as claimed in claim 6 wherein the nylon-11 has a tensile strength within the range from 6,000 to 10,000 PSI, the polyether block amide has a tensile strength from 20 to 35 MPA, an elongation of 200 to 700%, and a shore hardness of 70A to 55D.

9. An intravascular catheter as claimed in claim 1 wherein the tubular body has one or more holes formed through the tubular wall adjacent to the one end thereof which is fused to the soft tip.

10. An intravascular catheter as claimed in claim 1 wherein the soft flexible tip is fused to the one end of the tubular body by means of a butt-joint.

* * * * *